US007560117B2

(12) United States Patent
Hughes et al.

(10) Patent No.: US 7,560,117 B2
(45) Date of Patent: Jul. 14, 2009

(54) FOAMY VIRUS MUTANT REVERSE TRANSCRIPTASE

(75) Inventors: Stephen Hughes, Smithsburg, MD (US); Paul Boyer, Greencastle, PA (US); Maxine Linial, Seattle, WA (US); Carolyn Stenbak, Gif-sur-Yvette (FR); Patrick Clark, Frederick, MD (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 78 days.

(21) Appl. No.: 10/478,442

(22) PCT Filed: May 22, 2002

(86) PCT No.: PCT/US02/16528

§ 371 (c)(1),
(2), (4) Date: Nov. 21, 2003

(87) PCT Pub. No.: WO02/095004

PCT Pub. Date: Nov. 28, 2002

(65) Prior Publication Data

US 2004/0132009 A1    Jul. 8, 2004

Related U.S. Application Data

(60) Provisional application No. 60/292,994, filed on May 22, 2001.

(51) Int. Cl.
    *A61K 39/12*     (2006.01)
    *A61K 39/21*     (2006.01)
(52) U.S. Cl. .............. 424/207.1; 424/199.1; 424/204.1; 424/205.1
(58) Field of Classification Search ........................ None
    See application file for complete search history.

(56) References Cited

U.S. PATENT DOCUMENTS 4,873,192 A    10/1989  Kunkel
5,929,222 A *   7/1999  Lindemann et al. ........ 536/23.4

OTHER PUBLICATIONS

Konvalinka et al. Active Foamy Virus Proteinase Is Essential for Virus In Infectivity but Not for Formation of a Pol Polyprotein, Journal of Virology, Nov. 1995, vol. 69, No. 11, pp. 7264-7268.*
Pfrepper et al. Molecular Characterization of Proteolytic Processing of the Pol Proteins of Human Foamy Virus Reveals Novel Features of the Viral Protease, Journal of Virology, Sep. 1998, vol. 72, No. 9, pp. 7648-7652.*
Lochelt et al. The Human Foamy Virus pol Gene Is Expressed as a Pro-Pol Polyprotein and Not as a Gag-Pol Fusion Protein, Journal of Virology, Feb. 1996, vol. 70, No. 2, pp. 1033-1040.*
NCBI Entrez Genome [online], Human Foamy Virus, complete genome, Reference sequence No. NC 001736, GenBank No. Y07725, Oct. 8, 1996 [retrieved Jul. 31, 2007]. 5 pages.*

Achong et al., "An Unusual Virus In Cultures From A Human Nasopharyngeal Carcinoma", *J. Natl. Cancer Inst.* 42:299-307 (1971).
Baldwin and Linial, "Proteolytic Activity, The Carboxy Terminus Of Gag, And The Primer Binding Site Are Not Required For Pol Incorporation Into Foamy Virus Particles", *J. Virol.* 73:6387-6393 (1999).
Boyer and Hughes, "Analysis Of Mutations At Position 184 In Reverse Transcriptase Of Human Immunodeficiency Virus Type 1", *Antimicrobial Agents Chemother.*, 39:1624-1628 (1995).
Boyer and Hughes, "Effects Of Amino Acid Substitutions At Position 115 On The Fidelity Of Human Immunodeficiency Virus Type 1 Reverse Transcriptase", *J. Virol.* 74:6494-6500 (2000).
Boyer et al., "YADD Mutants Of Human Immunodeficiency Virus Type 1 And Moloney Murine Leukemia Virus Reverse Transcriptase Are Resistant To Lamivudine Triphosphate (3TCTP) In Vitro", *J. Virol.* 75:6321-6328 (2001).
Ding et al., "Protein-Nucleic Acid Interactions And DNA Conformation In A Complex Of Human Immunodeficiency Virus Type 1 Reverse Transcriptase With A Double-Stranded DNA Template-Primer," *Biopolymers* 44:125-138 (2000).
Fabricant et al., "Feline Viruses. XI. Isolation Of A Virus Similar To A Myxovirus From Cats In Which Urolithiasis Was Experimentally Induced", *Cornell Vet.* 59:667-672 (1969).
Gao et al., "The Role Of Steric Hindrance In 3TC Resistance Of Human Immunodeficiency Virus Type-1 Reverse Transcriptase", *J. Mol. Biol.* 300:403-418 (2000).
Halvas et al., "Development Of An In Vivo Assay To Identify Structural Determinants In Murine Leukemia Virus Reverse Transcriptase Important For Fidelity", *J. Virol.* 74:312-319 (2000).
Harris et al., "Functional Analysis of Amino Acid Residues Constituting the dNTP Binding Pocket of HIV-1 Reverse Transcriptase", *J. Biol. Chem.* 273:33624-33634 (1998).
Heinkelein et al., "Complex Effects Of Deletions In The 5' Untranslated Region Of Primate Foamy Virus On Viral Gene Expression And RNA Packaging", *J. Virol.* 74:3141-3148 (2000).
Herchenroder et al., "Isolation, Cloning, And Sequencing Of Simian Foamy Viruses From Chimpanzees (SFVcpz): High Homology To Human Foamy Virus (HFV)", *Virology* 201:187-199 (1994).

(Continued)

*Primary Examiner*—Bruce Campell
*Assistant Examiner*—Sharon Hurt
(74) *Attorney, Agent, or Firm*—Townsend and Townsend and Crew LLP

(57) ABSTRACT

The present invention relates to a highly processive reverse transcriptase having DNA polymerase activity and substantially reduced protease activity. More specifically, the invention relates to an isolated reverse transcriptase from foamy virus comprising a substantially inactivated protease. The invention also relates to vectors containing the gene and hosts transformed with the vector of the invention. Further, the invention relates to a method for producing reverse transcriptase having DNA polymerase activity and substantially reduced protease activity by expressing the reverse transcriptase genes of the present invention in a recombinant host. Methods are also provided for producing cDNA from polynucleotides using the highly processive reverse transcriptase of the invention. Kits for the preparation of cDNA from RNA comprising the highly processive reverse transcriptase of the invention are also provided.

5 Claims, 2 Drawing Sheets

OTHER PUBLICATIONS

Hooks and Detrick-Hooks, "Spumavirinae: Foamy Virus Group Infections: Comparative Aspects And Diagnosis," In Kurstak and Kurstak (eds.), Comparative Diagnosis of Viral Diseases, vol. 4, pp. 599-619, *Academic Press, Inc.*, New York (1981).

Hruska and Takemoto, "Biochemical Properties Of A Hamster Syncytium-Forming ("Foamy") Virus," *J. Natl. Cancer Inst.* 54:601-605 (1975).

Huang et al., "Structure Of A Covalently Trapped Catalytic Complex Of HIV-1 Reverse Transcriptase: Implications For Drug Resistance", *Science* 282:1669-1675 (1998).

Jacobo-Molina et al., "Crystal Structure Of Human Immunodeficiency Virus Type 1 Reverse Transcriptase Complexed With Double-Stranded DNA At 3.0 Å Resolution Shows Bent DNA", *Proc. Natl. Acad. Sci USA* 90:6320-6324 (1993).

Julias et al., "Replication Of Phenotypically Mixed Human Immunodeficiency Virus Type 1 Virions Containing Catalytically Active And Catalytically Inactive Reverse Transcriptase", *J. Virol.* 75:6537-6546 (2001).

Kogel et al., "Molecular Biological Characterization Of The Human Foamy Virus Reverse Transcriptase And Ribonuclease H Domains", *Virology* 213:97-108 (1995).

Kohlstaedt et al., "Crystal Structure At 3.5 Å Resolution Of HIV-1 Reverse Transcriptase Complexed With An Inhibitor", *Science* 256:1783-1790 (1992).

Konvalinka et al., "Active Foamy Virus Proteinase Is Essential For Virus Infectivity But Not For Formation Of A Pol Polyprotein", *J. Virol.* 69:7264-7268 (1995).

Lochelt et al., "Construction Of An Infectious DNA Clone Of The Full-Length Human Spumaretrovirus Genome And Mutagenesis Of The *bel* 1 Gene", *Virology* 184:43-54 (1991).

Moebes et al., "Human Foamy Virus Reverse Transcription That Occurs Late In The Viral Replication Cycle", *J. Virol.* 71:7305-7311 (1997).

Malmquist et al., "Isolation, Immunodiffusion, Immunofluorescence, And Electron Microscopy Of A Syncytial Virus Of Lymphosarcomatous And Apparently Normal Cattle", *Cancer Res.* 29:188-200 (1969).

Mauer et al., "Analysis Of The Primary Structure Of The Long Terminal Repeat And The *Gag* and *Pol* Genes Of The Human Spumaretrovirus", *J. Virol.* 62:1590-1597 (1988).

Moebes et al., "Human Foamy Virus Reverse Transcription That Occurs Late In The Viral Replication Cycle", *J. Virol.* 71:7305-7311 (1997).

Nanni et al., "Review Of HIV-1 Reverse Transcriptase Three-Dimensional Structure: Implications For Drug Design", *Perspect. Drug Discov. Des.* 1:129-150 (1993).

Pfrepper et al., "Characterization Of Peptide Substrates And Viral Enzyme That Affect The Cleavage Site Specificity Of The Human Spumaretrovirus Proteinase", *Virus Genes* 22:61-72 (2001).

Pfrepper et al., "Molecular Characterization Of Proteolytic Processing Of The Pol Proteins Of Human Foamy Virus Reveals Novel Features Of The Viral Protease", *J. Virol.* 72:7648-7652 (1998).

Rethwilm, "Regulation Of Foamy Virus Gene Expression", *Curr. Top. Microbiol. Immunol.* 193:1-24 (1995).

Sarafianos et al., "Lamivudine (3TC) Resistance In HIV-1 Reverse Transcriptase Involves Steric Hindrance With β-Branched Amino Acids", *Proc. Natl. Acad. Sci USA* 96:10027-10032 (1999).

Schinazi et al., "Characterization Of Human Immunodeficiency Viruses Resistant To Oxathiolane-Cytosine Nucleosides", *Antimicrobial Agents Chemother.* 37:875-881 (1993).

Tantillo et al., "Locations Of Anti-AIDS Drug Binding Sites And Resistance Mutations In The Three-Dimensional Structure Of HIV-1 Reverse Transcriptase", *J. Mol. Biol.* 243:369-387 (1994).

Taylor et al., "The Use Of Phosphorothioate-Modified DNA In Restriction Enzyme Reactions To Prepare Nicked DNA", *Nucl. Acids Res.* 13:8749-8764 (1985).

Taylor et al., "The Rapid Generation of Oligonucleotide-Directed Mutations at High Frequency Using Phosphorothioate-Modified DNA", *Nucl. Acids Res.* 13:8765-8785 (1985).

Telesnitsky and Goff, "Two Defective Forms Of Reverse Transcriptase Can Complement To Restore Retroviral Infectivity", *EMBO J.* 12:4433-4438 (1993).

Tisdale et al., "Rapid In Vitro Selection Of Human Immunodeficiency Virus Type 1 Resistant To 3'-Thiacytidine Inhibitors Due To A Mutation In The YMDD Region Of Reverse Transcriptase", *Proc. Natl. Acad. Sci. USA* 90:5653-5656 (1993).

Vogt and Simon, "Mass Determination Of Rous Sarcoma Virus Virions By Scanning Transmission Electron Microscopy", *J. Virol.* 73:7050-7055 (1999).

Yu et al., "Evidence That The Human Foamy Virus Genome Is DNA", *J. Virol.* 73:1565-1572 (1999).

Yu et al., "Human Foamy Virus Replication: A Pathway Distinct From That Of Retroviruses And Hepadnaviruses", *Science* 271:1579-1582 (1996).

Yu and Llnial, "Analysis Of The Role Of The *bel* And *bet* Open Reading Frames Of Human Foamy Virus By Using A New Quantitative Assay", *J. Virol.* 67:6618:6624 (1993).

\* cited by examiner

FOAMY VIRUS MUTANT REVERSE TRANSCRIPTASE

RELATED APPLICATIONS

This application is a 35 U.S.C. § 371 United States National phase application of PCT/US02/16528, filed May 22, 2002, which claims priority to United States Patent Application Ser. No. 60/292,994, filed May 22, 2001, incorporated herein by reference in its entirety.

STATEMENT AS TO RIGHTS TO INVENTIONS MADE UNDER FEDERALLY SPONSORED RESEARCH AND DEVELOPMENT

This work was supported by a grant from the National Cancer Institute (No. CA18282 and CA09229)

BACKGROUND OF THE INVENTION

Foamy Viruses (FVs; Spumavirinae) are classified as retroviruses and demonstrate classic retroviral genomic organization, including the three hallmark genes gag, pol, and env (FIG. 1; Rethwiln, *Curr. Top. Microbiol. Immunol.* 193:1-24 (1995)). Despite this classification and organization, several aspects of the FV life cycle differ significantly from retroviruses. Three of these differences highlight unique properties of the polymerase (Pol) protein and the reverse transcriptase (RT) enzyme encoded within it. First, FV has an unusual mechanism for the expression of Pol. Typical retroviruses express Pol as part of a Gag-Pol fusion protein, which mediates Pol incorporation into the virion through Gag-Gag interactions. In contrast, FV Pol is expressed from its own spliced message, and consequently FV must employ a unique strategy for incorporation of Pol into the viral particle (Lochelt and Flugel, *J. Virol.* 70:1033-1040 (1996), Yu et al. *Science* 271:1579-1582 (1996)). Second, reverse transcription occurs at a different stage in the FV life cycle. Unlike conventional retroviruses, FV particles contain DNA that appears to be used as the functional genome when infecting a new cell (Moebes et al., *J. Virol.* 71:7305-7311 (1997), Yu et al., *J. Virol.* 73:1565-1572 (1999)). This requires that FV RT be active during, or shortly after particles bud from an infected cell. Third, the FV Pol polyprotein undergoes limited processing. A single cleavage event between RT and Integrase (IN) takes place resulting in two mature enzymatic proteins, IN and a PR-RT fusion protein (Pfrepper et al., *Virus Genes* 22:61-72 (2001)).

Because of its central role in the retroviral life cycle, RT has been a target of drugs designed to inhibit HIV-1 replication and control infections. One major class of these RT inhibitors is the nucleoside analog inhibitors, or chain terminators, which include (AZT) and (3TC). In vitro, these drugs have proven to be potent inhibitors of RT activity and viral replication for many retroviruses, including HIV-1. However, it has been demonstrated previously that of 3TC, AZT, and ddI, only AZT specifically inhibits SFVcpz (hu), (a human foamy virus newly designated Prototype Foamy Virus (PFV)), replication (Yu et al., *J. Virol.* 73:1565-1572 (1999)).

In HIV-1 patients, these drugs have been shown to inhibit viral replication, but HIV-1 is able to rapidly evolve mutations that allow it to overcome this inhibition. In the case of 3TC, resistance rapidly and consistently develops through mutation of the second residue in the HIV-1 catalytic motif Tyr Met Asp Asp (YMDD) to valine (Tisdale et al. *Proc. Natl. Acad. Sci. USA* 90:5653-5656 (1996)). The YXDD (SEQ ID NO: 17) catalytic motif, wherein X defines any amino acid residue, is highly conserved among all reverse transcriptases, and all retroviral RTs contain a methionine in the second residue with the exception of Murine Leukemia Viruses (MLVs) and FVs, which contain a valine in this position. When the amino acid sequence of SFVcpz(hu) RT (PFV RT) is compared to other retroviral RTs, the degrees of homology range from about 27% (HIV-2) to about 34% (Mo-MLV) (Maurer et al. *J. Virol.* 62:1590-1597 (1988)). Despite this low level of overall homology, PFV RT contains residues shown to be functionally essential in all other retroviral RTs, including the YXDD motif (SEQ ID NO: 17). Interestingly, both MLV and FV contain a valine in their catalytic YXDD motifs (SEQ ID NO: 17), and both are naturally resistant to 3TC.

In the context of the virus, RT is expressed as part of a larger Pol polyprotein, which also contains Integrase (INT) and Protease (PR). Unlike other retroviruses, the FV Pol undergoes a single cleavage event to release INT, leaving a mature PR-RT fusion protein. However, in bacterial overexpression systems a second cleavage event between PR and RT has been previously observed. To avoid this artificial cleavage, as provided herein the entire PR-RT fusion protein was bacterially expressed with a point mutation in the PR active site termed D/A, wherein an alanine replaces an aspartic acid residue. Both wild type and a mutated (V313M) RTs were successfully expressed and purified in the D/A context.

Further, it was determined from mutations in the RT which reduce the activity of the RT by about 45 to 60% that foamy virus (FV) production was inhibited or stopped when RT activity was reduced. Therefore, unlike other retroviruses FV requires a highly active reverse transcriptase. It has also been determined by the present invention that FV requires a reverse transcriptase that is highly processive, i.e., capable of producing long nucleotide transcription products. In one embodiment of the present invention an isolated FV RT has been found to be capable of generating products that were well above 600 base pairs(bp) in 10 minutes. In similar studies the processivity of HIV-1 reverse transcriptase has been measured to generate transcript products of 150 bp or smaller (Boyer and Hughes, *Microbiol. Agents Chemother.* 39:1624-8 (1995)).

BRIEF SUMMARY OF THE INVENTION

The present invention relates to an isolated foamy virus protease-reverse transcriptase polyprotein having highly processive reverse transcriptase activity and substantially reduced protease activity. In particular, the invention relates to polyproteins wherein the nucleic acid which encodes the foamy virus protease-reverse transcriptase has been mutated so as to functionally inactivate the protease activity. In one particular embodiment the nucleic acid sequence that encodes the aspartic acid in the catalytic site of the protease is changed, for example, to encode alanine.

The invention also provides for the production of the isolated foamy virus protease-reverse transcriptase having DNA polymerase activity and substantially reduced protease activity. Vectors and plasmids which comprise nucleic acids which encode the foamy virus protease-reverse transcriptase polyproteins and recombinant host cells are also disclosed. Kits for the production of cDNA from polynucleotides, e.g., RNA and the like, comprising containers having a foamy virus protease reverse transcriptase of the present application, a primer, nucleotide triphosphates and the necessary buffers comprise another embodiment of the invention.

DESCRIPTION OF THE SPECIFIC EMBODIMENTS

Figure 1:
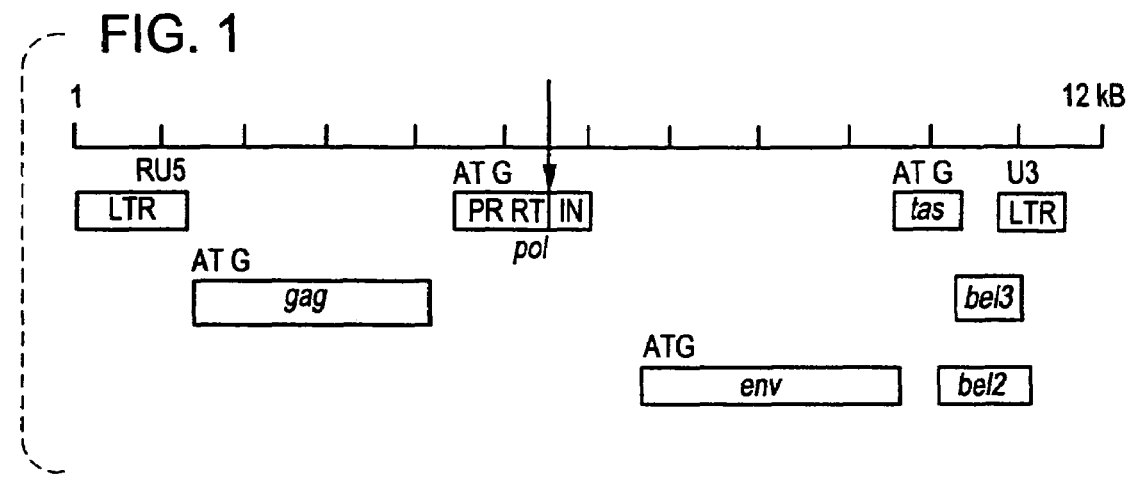
FIG. 1 provides a schematic representation of the PFV genome and encoded proteins. Pfv is a complex retrovirus encoding six open reading frames (gray boxes). The Pol protein is synthesized independently of Gag and contains the enzymes protease, reverse transcriptase, and integrase. The arrow indicates the single Pol cleavage site.

The present invention relates to the production of an isolated highly active and highly processive foamy virus reverse transcriptase having DNA polymerase activity and substantially reduced protease activity. In particular, the isolated reverse transcriptase is a modified foamy virus protease-reverse transcriptase polyprotein having a functionally inactivated protease. Recombinant plasmids and vectors of the present invention provide for the production of the highly processive isolated reverse transcriptase for use in molecular and recombinant DNA methods, such as for the in vitro synthesis of cDNA from RNA, i.e., mRNA, to replace less processive enzymes used currently.

By the term "substantially no protease activity" is intended a purified or isolated foamy virus protease-reverse transcriptase (PR-RT) polyprotein or fusion protein having a functionally inactivated protease which does not cleave the foamy virus PR-RT fusion protein when overexpressed in a bacterial host cell.

The term "functionally inactivated" is intended to define point mutations and small amino acid deletions or insertions, i.e., up to 10 amino acid residues, in the protease of the foamy virus PR-RT fusion protein such that the protein retains high reverse transcriptase activity and has substantially reduced protease activity.

The foamy virus, or spumaviriae virus, reserve transcriptase can comprise a number of types, including for example, that isolated from nonhuman primates (Hooks and Detrick-Hooks, in Kurstak and Kurstak (eds.), *Comparative Diagnosis of Viral Disease*, Vol. 4, Academic Press, Inc., New York (1981), cows (Malanquist et al., *Cancer Res.* 16:188-200 (1969), cats (Fabricant et al., *Cornell Vet.* 59:667-672 (1969); hamsters (Hruska and Takemoto, *J. Natl. Cancer Inst.* 54:601-605(1975), and humans (Achong et al., *J. Natl. Cancer Inst.* 42:299-307 (1971), Mauer et al., *J. Virol.* 62:1590-1597 (1988)).

Reverse transcriptase (RT) of foamy virus appears to act as part of a protease-reverse transcriptase polyprotein or fusion protein in infected cells. Further, data indicates that the presence of the protease, or a portion thereof, contributes to the active structure of the reverse transcriptase. Unlike other retroviruses, FV Pol is expressed from is own spliced message. Although the mechanism for viral packaging the Pol must interact specifically with either the Gag protein, the genomic RNA, or both to ensure encapsidation.

PR-RT proviral DNA can be isolated using standard isolation techniques. The DNA can be cleaved or fragmented into linear segments. Fragmentation can be accomplished by, for example, use of enzymes which digest or cleave DNA, i.e., restriction enzymes, or mechanical forces. After fragmentation of the DNA, the segments are separated by standard methods. Description of such recombinant DNA methods can be found in, for example, Sambrook et al., *Molecular Cloning: A Laboratory Manual*, Second Edition, Cold Spring Harbor Laboratory Press, Cold Spring Harbor, N.Y. (1989) and Sambrook and Russell, *Molecular cloning: A Laboratory Manual*, Third Edition, Cold Spring Harbor Laboratory Press, Cold Spring Harbor, N.Y. (2001), each incorporated herein by reference.

The DNA fragments encoding the foamy virus PR-RT gene can be accomplished in any number of ways well known to the skilled artisan. For example, the DNA fragments can be referenced (Maxam and Gilbert, *Meth. Enzymol.* 64:499 (1980); Messing, *Meth. Enzymol.* 101C:20 (1983)). Alternatively, hybridization can be employed using a labeled, i.e., a radioactive, fluorescent, or luminescent label, DNA probe (Southern, *J. Mol. Biol.* 98: 503 (1975); Benton and Davis, *Science* 196:180 (1977); Grunstein and Hogness, *Proc. Natl. Acad. Sci. USA* 72: 3961-65 (1975)).

The identified fragments can be pooled, ligated into a suitable vector, used to transform or transfect a host cell. Transformed host cells are screened for production of PR and RT activity using methods well known to the skilled artisan as described herein. Alternatively, clones of transformed host cells can be screened and identified by hybridization with complimentary labeled oligonucleotide probes specific for the protease and reverse transcriptase gene.

In another embodiment, PR-RT nucleotide sequences further include derivatives (e.g., nucleotide sequence variants), such as those encoding other possible codon choices for the same amino acid or conservative substitutions thereof, such as, for example, naturally occurring allelic variants. Due to degeneracy of nucleotide coding sequences, other DNA sequences which encode substantially the same amino acid sequence as a foamy virus PR-RT can be used in the present invention. These include, but are not limited to, nucleotide sequences comprising substantially all or a portion of the gene encoding foamy virus PR-RT fusion protein having reverse transcriptase activity which is altered by the substitution of different codons that encode the same or a functionally equivalent amino acid residue (e.g. a conservative substitution) within the sequence, producing a silent change.

Foamy virus PR-RT nucleic acids further include those nucleic acids hybridizable to, or complementary to, the SFVcpz(hu) sequence (Herchenroder et al., *Virology* 201: 187-199 (1994), incorporated herein by reference in its entirety). This isolate has been recently designated Prototype Foamy Virus (PFV) and this designation will be used throughout the present disclosure. In a specific embodiment, a nucleic acid that is hybridizable to a foamy virus PR-RT nucleic acid, or to a nucleic acid encoding a foamy virus PR-RT derivative, under conditions of low, medium or high stringency is provided. Low, moderate, and high stringency conditions are well known to those of skill in the art, and will vary predictably depending on the base composition of the particular nucleic acid sequence and on the specific organism from which the nucleic acid is derived. For guidance regarding such conditions see, for example, Sambrook et al., (1989) supra, incorporated herein by reference.

An alternative to isolating the PR-RT gene from a foamy virus proviral DNA is to synthesize the nucleic acid by standard methods well known in the art (e.g., by use of a commercially available automated DNA synthesizer).

In another embodiment, polymerase chain reaction (PCR) can be used to amplify the desired sequence in a genomic or cDNA library, prior to selection. Oligonucleotide primers representing known foamy virus PR-RT sequences can be used as primers in PCR. The synthetic oligonucleotide can be utilized as primers to amplify particular oligonucleotides within the FV PR-RT gene by PCR sequences from a source (RNA or DNA), typically a cDNA library, of potential interest. PCR can be carried out, for example, by use of a Perkin-Elmer Cetus thermal cycler and Taq polymerase (Gene Amp). The DNA being amplified can include mRNA or cDNA or genomic DNA.

The identified and isolated FV PR-RT nucleic acids encoding a PR-RT polyprotein having substantially reduced protease activity can then be inserted into an appropriate cloning vector. A large number of vector-host systems known in the art can be used. Possible vectors include, but are not limited to, plasmids or modified viruses. The vector system is selected to be compatible with the host cell. Such vectors include, but are not limited to, bacteriophages such as lambda derivatives, yeast integrative and centromeric vectors, 2µ plasmid, and derivatives thereof, or plasmids such as pT5m, pBR322, pUC, pcDNA 3.1 or pRSET (Invitrogen) plasmid derivatives or the Bluescript vector (Stratagene) to name a few. The insertion of the FV PR-RT nucleic acid of the present invention into a cloning vector can, for example, be accomplished by ligating the nucleic acid, e.g. DNA, fragment into a cloning vector that has complementary cohesive termini. If the complementary restriction sites used to fragment the DNA are not present in the cloning vector, however, the ends of the DNA molecules can be enzymatically modified. Alternatively any desired restriction endonuclease site can be produced by ligating nucleotide sequences (e.g., linkers) onto the DNA termini, these ligated sequences can comprise specific chemically synthesized oligonucleotides encoding restriction endonuclease recognition sequences. In an alternative method, the cleaved vector and FV PR-RT nucleic acids can be modified by homopolymeric tailing. Recombinant molecules can be introduced into host cells by, for example, transformation, transfection, infection, electroporation, and the like, so that many copies of the nucleic acid sequence are generated.

The nucleic acid encoding FV PR-RT of the present invention or a functionally active derivative thereof can be inserted into an appropriate expression vector, i.e., a vector that contains the necessary elements for the transcription and translation of the inserted polypeptide coding sequence. The necessary transcriptional and translational signals can also be supplied by the native FV PR-RT gene and/or its flanking regions. A variety of host-vector systems can be utilized to express the FV PR-RT polyprotein or fusion protein. These include, but are not limited to, mammalian cell systems infected with virus, (e.g., vaccinia, adenovirus, modified foamy virus, and the like), insect cell systems infected with virus, e.g., baculovirus, microorganisms such as yeast, or transformed bacteria. The expression elements of vectors vary in their strength and specification. Depending on the host-vector system utilized, any one of a number of suitable transcription and translation elements can be used. In a specific embodiment, the PFV PR-RT of the present invention is expressed, or a nucleic acid sequence encoding a functionally active reverse transcriptase and a functional inactive protease is expressed in mammalian cells or bacteria.

Any of the methods previously described for the insertion of oligonucleic acid (ONA) fragments into a vector can be used to construct expression vectors containing a chimeric gene consisting of appropriate transcriptional translational control signals and the polyprotein coding sequences. These methods include in vitro recombinant DNA and synthetic methods and in vitro recombinants (genetic recombination). Expression of nucleic acid sequences encoding the FV PR-RT fusion protein of the present invention can be regulated by a second nucleic acid sequence so that the FV PR-RT of the invention is expressed in a host transformed with the recombinant DNA molecule. For example, expression of a FV PR-RT polyprotein can be controlled by any promoter/enhancer element known in the art. Promoters that can be used include, but are not limited to, the SV40 early promoter region (Benoint and Chambon, *Nature* 290:304-310(1981)), the promoter contained in the 3' long terminal repeat of *Rous sarcoma* virus (Yamamoto et al., *Cell* 22:787-797 (1980)), the herpes thymidine kinase promoter (Wagner et al., *Proc. Natl. Acad. Sci. USA* 78:1441-1445(1981)), the regulatory sequences of the metallothionein gene (Brinster et al., *Nature* 296:3942 (1982)), prokaryotic expression promoters such as β-lactamase promoter (Villa-Komanoff et al., *Proc. Natl. Acad. Sci. USA* 75:3727-3731 (1978)) or the tac promoter (deBoer et al., *Proc. Natl. Acad. Sci. USA* 80: 21-25 (1983)), just to name a few.

Expression vectors containing FV PR-RT nucleic acid inserts of the present invention can be identified by general approaches well know to the skilled artisan, including: (a) nucleic acid hybridization, (b) the presence or absence of "marker" gene function, and (c) expression of the encoded FV PR-RT fusion protein having a substantially functionally inactive protease and an active reverse transcriptase. Once a particular recombinant DNA molecule is identified and isolated, several methods well known to the skilled artisan can be used for propagation. Once a suitable host system and growth conditions are established, recombinant expression vectors can be propagated and prepared in quantity.

In order to prepare a nucleic acid that encodes FV PR-RT having high processivity and a substantially inactive protease the FV PR-RT gene, or nucleic acid, can be mutagenized to create a substitution, deletion or insertion in the protease sequence. In a specific embodiment, an Aspartic acid (Asp, D) residue in the protease catalytic site was replaced by an Alanine (Ala; A) residue by altering the codon that encodes the Aspartic acid residue. This can be accomplished, for example, by site-directed mutagenesis using the Amersham technique (Amersham mutagenesis kit, Amersham, Inc., Cleveland, Ohio) based on the methods of Taylor et al., *Nucl. Acids Res.* 13: 8749-8764 (1985); Taylor et al., *Nucl. Acids Res.* 13: 8764-8785 (1985); Nakamaya and Eckstein, *Nucl. Acids Res.* 14: 9679-9698 (1986); Dente et al., *DNA Cloning*, Glover ed., IRL Press, p. 791-802 (1985); using a Promega kit (Promega, Inc., Madison, Wis.); or using a BioRad kit (Bio-Rad, Inc., Richmond, Calif.), based on the methods of Kunkel (*Proc. Natl. Acad. Sci. USA* 82:488-492 (1985); *Meth. Enzy-*

*mol.* 154:367-382(1987); U.S. Pat. No. 4,873,192), all of which are incorporated herein by reference.

Site directed mutagenesis can also be accomplished using PCR-based mutagenesis such as that described by Zheng bin et al. (in *PCR Methods and Applications*, Cold Spring Harbor Laboratory Press, Cold Spring Harbor, N.Y., pp. 205-207 (1992), Jones and Howard (*BioTechniques* 8: 178-183(1990); *Biotechniques* 10:12-66 (1991); Ho et al., *Gene* 77: 61-68 (1989). Other methods of mutagenizing a FV PR-RT gene to substantially reduce protease activity, including chemical and radiation methods, are known to the skilled artisan and considered within the scope of the present invention.

The invention also relates to fusion proteins which comprise the FV PR-RT of the invention. Such fusion protein can comprise, for example, the FV PR-RT and (a) a leader amino acid sequence incorporated to direct secretion of the polyprotein out of a host cell, (b) an amino acid sequence added to aid in purification of the FV PR-RT polyprotein, e.g., a polyhistidine sequence, or (c) additional polypeptides of the foamy virus Pol open reading frame including the Integrase and/or RNaseH. The Integrase and/or RNaseH polypeptides can be active or functionally inactivated.

The FV PR-RT polyprotein of the present invention can be isolated and purified by standard methods, including chromatography (e.g. ion exchange, affinity, sizing or high pressure liquid chromatography), centrifugation, differential solubility, or by any other standard technique for the purification of protein. The functional properties can be evaluated using any suitable assay as described herein or otherwise known to the skilled artisan. The polyprotein can also be synthesized by standard chemical methods known in the art (see, e.g., Hunkapiller et al., *Nature* 310:105-111 (1984); Stewart and Young, *Solid Phase Peptide Synthesis*, $2^{nd}$ ed., Pierce Chemical Company, Rockford, Ill. (1984)).

The isolated FV PR-RT polyprotein having high processivity and substantially reduced protease activity produced by any of the above described methods can be used to prepare cDNA from RNA by, for example, hybridizing an oligo (dT) primer or other complimentary primer with the RNA. The synthesis of a complete cDNA can be accomplished by adding the FV PR-RT and all four deoxynucleotide triphosphates. Using the FV PR-RT of the present invention allows for high processivity. In a specific embodiment, the expressed FV PR-RT was highly active and processed nucleic acid sequences longer than that produced by wild-type HIV-1 in a similar assay.

In addition, the isolated FV PR-RT of the present invention has a high fidelity of transcription of a template sequence. "High" in the context of the present invention is intended to mean that the isolated FV PR-RT of the present invention has an error rate of at least two-fold lower than the HIV-1 reverse transcriptase in the same fidelity assay. In a specific embodiment of the present invention, the FV PR-RT has a error rate of about five-fold less than that measured for HIV-1 RT. A standard fidelity assay is described, for example, in Boyer and Hughes, (*J. Virol.* 74:6494-6500 (2000) incorporated herein by reference). The fidelity assay involves the copying of a DNA segment that encodes the α-complementing peptide of *E. coli* β-galactosidase. Single-stranded template DNA is isolated from a bacterial strain that incorporates deoxyruracil into DNA, such as plasmid Litmus 29 (Not) from a Dut$^-$ *E. coli* strain. The template U-DNA is hybridized to a primer, which is extended in vitro by the RT to be tested, i.e., FV wild-type or FV mutant RT, or HIV-1 RT, and the like, so that the DNA segment encoding the α-complementing peptide is copied. The resulting double-stranded DNA is digested, and the fragment containing the LacZα coding region is ligated to a plasmid and introduced into a Dut$^+$ Ung$^+$ *E. coli* strain, which ensures that the DNA strand synthesized in vitro by the RT being tested is preferentially retained and copied, giving rise to the plasmids subsequently isolated from individual colonies. The transformed *E. coli* is grown on plates containing an indicator for β-galactosidase activity (X-Gal). Colonies that are either white or light blue are counted and grown up, and the plasmids recovered. Segments encoding the LacZα peptide are sequenced. In this assay, a percentage of mutations are silent, therefore the method necessarily underestimates the actual error rate. The lacZα RNA transcript from Litmus 29 (Not) encodes a fusion protein. The LacZα peptide is the C-terminal part of the fusion protein; the N terminus, which makes no functional contribution to LacZα activity, is derived from the polylinker. A small part of the N-terminal region of this fusion protein is encoded with the NotI/BamHI fragment generated in vitro by RT. Because this region does not encode a functional part of LacZα, only mutations that create termination codons or frameshift mutations will be detected, potentially skewing the results. Therefore, only mutations are scored within the 174-bp region from the glycine codon GGA, which is the junction point between lacZα and the polylinker and the first termination codon at the end of lacZα. The result of the fidelity assay for FV RT is compared with the result for HIV-1 RT to determine whether the RT has a "high" fidelity.

The FV PR-RT of the present invention is ideally suited for incorporation into a kit for the preparation of cDNA from a polynucleotide sequence, i.e., single-stranded DNA, RNA and the like. Kits are well known in the art and typically can comprise a container means being compartmentalized to receive a close confinement therein, such as vials, tubes, and the like, each container means comprising one of the separate elements of the method used to prepare cDNA from a polynucleotide sequence. For example, there can be provided a container means containing FV PR-RT polyprotein in solution. Further, container means can contain suitable buffers, substrates for DNA synthesis such as deoxynucleoside triphosphates, oligo(dT) or complementary primer, and control RNA for use as a standard.

The following examples are illustrative and are not intended to be limiting of the methods or compositions of the present invention. Any suitable modifications and adaptations which are obvious to one of ordinary skill in the art are within the scope of the present invention.

EXAMPLES

The present example describes the construction of a mutant prototype foamy virus reverse transcriptase having a methionine in place of a valine in the catalytic site of the enzyme. Further, the example provides the construction of a mutant polymerase-reverse transcriptase mutant fusion protein comprising a mutation in the active site of the polymerase both with and without the mutation in the catalytic site of the reverse transcriptase. These constructs were used to transfect host cells and demonstrate the overproduction of the gene products. The PR-RT fusion protein comprising an inactive protease and wild-type reverse transcriptase was demonstrated to be not only highly active and processive, but also to produce a RT of high fidelity. The mutant PR-RT polyprotein comprising the protease with substantially reduced activity and mutated reverse transcriptase was not as active as wild-type reverse transcriptase, but was still more active than the RT of many other retroviruses, including HIV-1 reverse transcriptase.

Materials and Methods

Construction of Prototype Foamy Virus (PFV) RT-V313M Mutant. The shuttle vector pL2-Sub2 (Baldwin and Linial, *J. Virol.* 73:6387-6393 (1999)) was used to change the valine residue of the Tyr Xaa Asp Asp (YXDD; SEQ ID NO: 17) motif of SFVcpz(hu) (PFV) reverse transcriptase catalytic site to a methionine. (Tyr Val Asp Asp (YVDD; SEQ ID NO: 17) to Tyr Met Asp Asp (YMDD; SEQ ID NO: 17). The mutagenic oligonucleotide polV313M was designed as a forward primer to change nucleotides 1682-1684 from GTT to ATG to create the Valine (V) to Methionine (M) mutation, and change nucleotides 1694-1696 from TAT to TAC to create a unique AflII site to be used for screening (5'-CTAATGTACAAGTGTATAT GGATGATATATACTTAAGCCATG-3'; SEQ ID NO: 1). The reverse primer Int(−) corresponds to nucleotides 2440-2459 of pL2-Sub2 (5'-CCCCAGGCTTTACACTTTATG-3'; SEQ ID NO: 2). Using these primers and the pL2-Sub2 template, PCR mutagenesis was used to generate a 794 base pair (bp) fragment that was digested with BsrGI and XbaI and cloned back into the pL2-Sub2 vector. Clones were screened with AflII to indicate the presence of the mutated insert and two were identified. Appropriate segments from these two clones were moved back into the full-length PFV molecular clone context of pHFV13 by PacI/SwaI digestion and which were sequenced to verify the presence of the mutations. The resulting plasmids were named PFV RT-V313M(A) and RT-V313M(B).

Tissue Culture Methods. FAB cells (BHK cells containing HFV LTR-β-Gal DNA)(Yu and Linial, *J. Virol.* 67:6118-6624 (1993) and 293T cells were grown in Dulbecco modified Eagle (DME) medium with 10% fetal calf serum. Transfections of FAB cells were performed using LIPOFECTAMINE reagent (GIBCO-BRL, Gaithersburg, Md.) according to the manufacturer's instructions (Yu et al., *J. Virol.* 73:1565-1572 (1999), incorporated herein by reference). Briefly, FAB cells were plated at a density of $9\times10^5$ in a 10 cm-diameter tissue culture dish. The next day, cells were transfected according to the manufacturer's instructions. Briefly, the transfection mixture contained 25 μl LIPOFECTAMINE reagent and 10 μg of plasmid DNA. Lipid/DNA complexes were left on the cells 3 hrs, then removed and replaced with fresh media. Transfection of 293 cells was performed using a Calcium Phosphate method (Chen and Okayama, *Mol. Cell. Biol.* 7:2745-2752 (1987)).

Cell-free viral supernatants were obtained by filtration of supernatants through a 0.2 μm pore size filter. Intracellular virus was released by cell scraping, 3 freeze/thaw cycles, sonication for 15 sec, and centrifugation at 2000×g for 10 min. Virus were sedemented through a 20% sucrose cushion containing standard buffer (SB; 100 mM NaCl, 10 mM Tris, 1 mM EDTA, (pH 8.0), 20% sucrose) by centrifugation at 24,000 rpm at 4° C. for 2 hr. Pellets were resuspended in SB with 10 mM $MgCl_2$ and DNase-treated with RQ-1 RNase-free DNase (Promega, Madison, Wis.) (1 μl per 50 μl sample volume) at 37° C. for 1 hr. For polymerase assays, viral supernatants were concentrated to 1/100 (1%) the original volume using Amicon CENTRIPREP C-50 spin columns.

A panel of reverse transcriptase inhibitors (Table 1) was tested at a series of concentrations and cell viability was analyzed for each at 24 hours post-treatment by trypan blue staining. The inhibition experiments were performed with the highest inhibitor concentration that did not affect cell viability. For pre-treatment with RT inhibitors, FAB cells were treated with inhibitor for 4 hrs and then infected with cell-free virus stocks suspended in medium containing inhibitor. Virus was left on the cells for 24 hrs, and the medium was removed and replaced with fresh medium containing inhibitor. The cells were fixed 48 hrs after infection and stained for β-gal activity. For post-treatment with RT inhibitors, FAB cells were infected with cell-free virus stocks suspended in medium without inhibitor. Twenty four hrs after infection, the medium was changed to fresh medium containing inhibitor and 48 hrs post-infection, virus was harvested and assayed for infectivity on fresh FAB cells (Yu and Linial, *J. Virol.* 67:6618-6624 (1993)).

Nucleic Acid Extractions. Extraction of DNA from viral particles was performed as previously described (Yu et al., *J. Virol.* 73:1565-1572 (1999)). Briefly, resuspended pellets were DNase treated, lysed with sodium dodecyl sulfate at a final concentration of 0.5%, extracted twice with a 24:24:1 mixture of phenol:chloroform:isoamyl alcohol, and nucleic acids were precipitated with ethanol. Pelleted nucleic acids were resuspended in the original volume of $dH_2O$ and treated with RNase A (Sigma) at 37° C. for 1 hr. The sample was then re-extracted as described and resuspended in the original volume of $dH_2O$.

Extraction of RNA from viral particles was performed by adding an equal mixture of phenol and 4 M guanidinium isothiocyanate at a 2:1 ratio to the concentrated virus sample. Samples were extracted twice with chloroform-isoamyl alcohol (24: 1) and nucleic acids were precipitated with ethanol in the presence of 10 μg of carrier glycogen (RNase-free; Boeringher Manheim). Pelleted nucleic acids were resuspended in the original volume of diethyl-pyrocarbonate (DEPC)-treated $dH_2O$ and treated with RQ-1 RNase-free DNase I (Promega) at 37° C. for 1 hr. The sample was then re-extracted as described and resuspended in the original volume of DEPC-treated $dH_2O$.

Extraction of genomic DNA was performed by scraping transfected cells into PBS, centrifuging the cell suspension at 2000×g for 10 min, resuspending the cells in PBS, and repeating the centrifugation. Cells were then resuspended in Digestion Buffer made with fresh proteinase K and RNase A (DB; 100 mM NaCl, 10 mM Tris-Cl (pH 8.0), 25 mM EDTA (pH8.0), 0.5% SDS, 100 μg/ml proteinase K, 1 μg/ml RNase A) and incubated at 50° C. overnight. 1M sodium perchlorate was added at half the sample volume, and the sample was phenol-chloroform extracted twice, followed by one chloroform extraction, as described above. The DNA was ethanol precipitated and resuspended in $dH_2O$.

Reverse Transcriptase-PCR, Cloning, and Sequencing of Revertants. Viral supernatants were pelleted by ultracentrifugation through a 20% sucrose cushion and viral RNA was extracted as described above. RNA was subjected to RT-PCR using forward primer pol1441+ (5'-CCAACACTCTGCTGGTATTTTAGCTACTA-3'; SEQ ID NO: 3) and reverse primer pol2351-(5'-CAGCTGACAAATTTGGACGTCCG-3'; SEQ ID NO: 4). PCR reaction mixtures contained 2.5 U of avian myeloblastosis virus reverse transcriptase (RT) (U.S. Biochemicals, Cleveland, Ohio), 6 U of RNase inhibitor (Boerhinger Mannheim, Indianapolis, Ind.), 1×PCR buffer (Perkin-Elmer, Branchburg, N.J.), 1.5 mM $MgCl_2$, 0.1 mM dNTP mix (Gibco-BRL, Grand Island, N.Y.), 1 U of Platinum Pfx DNA Pol (Gibco-BRL), and 4 ng of each primer. Samples were incubated at 42° C. for 45 min, followed by denaturation for 2 min at 95° C. before thermal cycling was done. Temperatures for denaturing, annealing, and extension were 95° C., 50° C., and 72° C. respectively for 45 sec, 45 sec, and 1 min each for 35 cycles. The final extension reaction was performed for 10 min at 72° C. RT-PCR products were purified using QIAEX II (Qiagen) and A-overhangs were added to the blunt ended products using 5 U PLATINUM TAQ (Gibco-BRL), 1×PCR buffer (Perkin-Elmer), 1.5 mM $MgCl_2$, and 0.1 mM dATP (Gibco-BRL) at 65° C. for 30 min. The DNA products were then cloned into the pGEM T EASY vector (Promega) and blue-white screening was used to identify clones containing the insert. White colonies were picked and sequenced using forward primer pol1548 (5'-GGTTAACAG-CATTTACCTGGCAAG-3'; SEQ ID NO: 5).

Virion-associated RT assays were performed using viral supernatants collected 4 days post-transfection of FAB cells and concentrated with CENTRIPREP 50 spin columns (Amicon). The substrate used in these assays was poly(A):d(T)$_{10}$ (Sigma). Concentrated viral supernatants were added to an RT cocktail containing final concentrations of 40 mM Tris-HCl(pH 8.0), 50 mM NaCl, 0.5 mM MnCl$_2$, 15 mM dTT, 25 mM each of dATP, dCTP, and dGTP, 0.1% NP-40, 2 µg/ml poly(A):d(T), and 0.25 µl/ml [α-$^{32}$P]-dTTP. Reactions were incubated at 37° C. for 90 min, taking time points at 30 min intervals. At each time point, 25 µl of the reaction was spotted onto DE81 filters and allowed to dry. Filters were washed 4 times at room temperature with 2×SSC for 5 min each, followed by 2 washes with 95% EtOH. Filters were then dried and counted in scintillation fluid.

Western Blots. Viral supernatants were concentrated as described above for the virion-associated RT assay. Concentrated virus was then added to SDS Sample Buffer and fractionated on a 10% SDS-PAGE gel. Proteins were transferred to an IMMOBILON-P membrane (Millipore, Bedford, Mass.) and reacted with antibodies according to standard protocols. The membrane was developed using ECL reagents (Amersham Pharmacia), and exposed to film.

2-LTR Circle—PCR. 100 ng of DNA was subjected to PCR using primers 350R (5'-AGAAGGGTCCATCTGAGT-CAC-3'; SEQ ID NO: 6) and 546F (5'-GATTAAGGTA TGAGGTGTGTGG-3'; SEQ ID NO: 7). Reaction conditions were 1×PCR buffer (Perkin-Elmer), 1.5 mM MgCl$_2$, 0.2 mM dNTP mix (Gibco-BRL), and 1 U Taq Polymerase. Samples were denatured at 95° C. for 5 min, followed by 30 cycles of denaturation, annealing, and extension at 95° C., 55° C., and 72° C. for 30 sec, 30 sec, and 1 min respectively. A final extension was carried out at 72° C. for 10 min. PCR products were fractionated on a 0.8% agarose gel and the gel was subjected to Southern Blotting as described below.

Southern Blots. 10 µg of DNA was digested with 40 Units of the restriction enzyme NcoI (New England Biolabs) overnight. The digested DNA samples were fractionated on a 0.9% agarose gel. The gel was washed and transferred to the Hybond membrane following standard protocols. The membrane was then UV cross-linked and pre-treated with Hybridization Buffer for 2 hrs at 42° C. (HB; 6×SSPE, 0.1% SDS, 20% Formamide, 100 ng/ml sheared salmon sperm DNA). Radiolabeled probe to the LTR region was generated with the PRIMEIT Random Priming Kit (Stratagene) using the BstEII-pHSRV13 fragment containing the LTR region. Membranes were incubated with radiolabeled probe in HB at 4° C. overnight. Blots were rinsed and exposed to film.

Construction of Prototype Foamy Virus Reverse Transcriptase Expression Clones. The construct RT2 pET16b (Kogel et al., *Virology* 213:97-108 (1995)) contains part of the PFV RT coding region but is missing the protease coding region and most of the RNase H domain. RTVM pET16b is similar except that the mutation V313M changes the polymerase active site motif from Tyr Val Asp Asp (YVDD;SEQ ID NO: 17) to Tyr Met Asp Asp (YMDD, SEQ ID NO: 17).

PCR amplification was used to generate DNA fragments containing the protease coding region and the RNaseH domain that could be linked to the PFV polymerase domain. The PCR amplification of the protease coding region used a 5' primer that generated an NcoI site at the ATG initiation codon (5'-GCGGCGCCATGGCGAATCCTCTTCAGCT-GTTACAGCCG CTTCCGGCGG-3'; SEQ ID NO: 8). The introduction of the NcoI site converted the start of the protease amino acid sequence from Met Asn Pro Leu Gln - - - (MNPLQ - - - ; SEQ ID NO: 18) to Met Ala Asn Pro Leu Gln - - - (MANPLQ - - - ; SEQ ID NO: 19). The 3' primer in the PCR amplification spans a unique AflIII restriction enzyme recognition sequence in the segment encoding the polymerase domain of PFV RT (5'GCGGCGCCTTGAG-GAAGACGTGTCCAA CAATACTGTTTACC-3'; SEQ ID NO: 9). This set of PCR primers was used for two separate PCR amplifications using different substrates: (i) one amplification used pHFV13 (Lochelt et al., *Virology* 184:43-54 (1991)), which is a full length, wild-type PFV clone; (ii) the second PCR amplification used PFV protease inactive (Konvalinka et al., *J. Virol.* 69:7264-7268 (1995)). The PCR products from these two amplifications were digested with NcoI; the 3' end remained blunt from the PCR amplification. The resulting 840 bp fragment was cloned as an NcoI/blunt end insert into NcoI/AftIII PFV and NcoI/AftIII Pfv D/A.

The RNaseH domain was also obtained by PCR amplification. The 5' primer in the amplification spanned a unique PflMI restriction endonuclease recognition site in the PFV pol domain (5' GCGGCGGGATCCGCTTTACCCATT-AGTGG ATAACATGGAT GAC 3'; SEQ ID NO: 10). The primer also generated a BamHI site 5' of the PflMI site. The 3' primer added a TAG termination codon after the tyrosine codon that normally marks the last amino acid in the RNaseH domain and also generated an EcoRI site 3' of the termination codon (5' GCGGCGGAATTCGCGCTAATATTGTTTGG <u>GATATC</u>CTTTTATATAAT GACCCTG 3'; SEQ ID NO: 11). The underlined sequence is a unique EcoRV restriction endonuclease recognition sequence present in the coding region. The PCR fragment was digested with BamHI/EcoRI and cloned into BamHI/EcoRI digested LITMUS-29. The clone, designated 3' PFV, contained the normal C-terminus of the PFV RNaseH domain.

To simplify protein purification, the C-terminus was further modified by the addition of six histidine residues before the termination codon. The unique EcoRV site was used as an entry point. The clone 3' PFV was digested with EcoRV and EcoRI, then ligated to synthetic DNA fragments to construct the clone 3' PFV (His). The synthetic DNA fragments were generated by kinasing oligonucleotide 1 (5'-ATCCCAAA-CAATATTCTT CCCATCATCACCACCATCATTAGTAG-GTACCCG-3'; SEQ ID NO: 12) and oligonucleotide 2 (5'-AATTCGGGTACCTTACTAATGATGGTGGTGATGATG GG AAGAATATTGTTTGGGAT-3'; SEQ ID NO: 13), followed by heating and slow cooling the oligonucleotides to allow them to anneal. The C-terminus of PFV RT is normally - - - ProLysGlnTyr ( - - - PKQY; SEQ ID NO: 14). In PFV (His) the coding region was altered so that the C-terminus was ProLysGlnTyrProSerSerGlyHisHisHisHisHisHis (- - - PKQYPSSGHHHHHH; SEQ ID NO: 15).

Three oligonucleotide fragments were ligated to generate clones containing all of the protease as well as the entire polymerase and RNaseH domains. The fragments were: a) the 840 bp NcoI/AftIII fragment from either NcoI/AftIII Pfv or NcoI/AftIII PFV D/A, which contain the active or inactive protease coding region respectively, b) the AftIII/PflMI fragment from either RT2 pET16b or RTVM pET16b, which contain the wild-type or V313M active site in the polymerase domain, and the PflMI/EcoRI fragment from 3' PFV (His). The fragments were co-ligated into NcoI/EcoRI digested LITMUS-29 to generate four clones: a) PFV (His), which has a wild-type protease and a wild-type RT; b) PFV D/A (His), which has an inactive protease and a wild-type RT; c) FV RTV313M (His), which has an active protease and the V313M mutation in the RT; and d) FV D/A RTV313M (His), which has an inactive protease and the V313M mutation in RT. For protein expression, the inserts were cloned into NcoI/EcoRI digested pT5m, which is similar in concept to the pET vectors. The clones were transformed into the Rosetta E. coli strain (Novagen, Madison, Wis.), a BL21 derivative. Only the clones that had the inactive protease expressed significant levels of protein in this system.

Protein Expression and Purification. Bacteria were grown at 37° C. with agitation to an O.D.600 nm of 0.5 to 0.6. Expression of the RT protein was induced by the addition of 0.2 μM IPTG and incubation of the bacteria for an additional 3 hr before harvesting. Fifty grams of pelleted bacteria was extracted in 100 ml of 50 mM $NaPO_4$, pH 8.0, 50 mM NaCl, 1.5 mM PMSF and 0.75 mg/ml lysozyme. The sample was incubated on ice for 30 min. 10.75 ml of 4 M NaCl was added to the suspension, followed by 3×30 sec sonication at 90% power (max. Watt 350) and 70% pulse. A ¾-inch probe was used with 5 min between each sonication. The suspension was centrifuged at 85,000×g for 90 min and the clear portion of the supernatant was removed. The remaining, somewhat viscous, portion of the supernatant was recentrifuged and the clear supernatant was collected. Supernatants were diluted 1:1 with 66 mM $NaPO_4$, pH 6.8, and 300 mM NaCl.

A 15 ml Q-Sepharose column and a 15 ml nickel column (Qiagen) were poured and connected in series with the Q column first. The columns were equilibrated with 50 mM $NaPO_4$, pH 7.0 and 300 mM NaCl. Diluted supernatants were loaded onto the columns at 1 ml/min. After loading, the columns were washed with equilibration buffer. After 100 ml of flow through, the Q column was removed and the nickel column was washed with an additional 150 ml of buffer. The Q column was next washed with 250 ml of 50 mM $NaPO_4$, pH 6.0, 10 mM imidazole, 300 mM NaCl, and 10% glycerol (w/v). A 150 ml×150 ml, 10 mM to 500 mM imidazole (in pH 6.0 buffer) gradient was used to elute the protein. Eight (8) ml fractions were collected. Fractions were pooled based on SDS-PAGE analysis. The resulting pool was between about 60 to 70 ml. This pool was divided in half, with each pool dialyzed versus 3×500 ml of 25 mM Tris acid/25 mM Tris base. Sample (50% of the pool) was removed from dialysis and centrifuged at 12,000×g for 30 min. The pellet was resuspended with 3 ml of 20 mM Hepes, pH 7.0, 100 mM imidazole, 300 mM NaCl, 1 mM EDTA and 10 mM DTT. One (1) ml of 2 M NaCl was added to the suspension, the sample was stirred for 30 min, and centrifuged at 12,000×g for 30 min.

The supernatant was loaded onto a 1.6 cm×85 cm Sephacryl 200 column (Amersham-Pharmacia) equilibrated with 20 mM Hepes, pH 7.0, 100 mM imidazole, 300 mM NaCl, 1 mM EDTA, and 1 mM DTT. The column was run at 0.2 ml/min with 10 min fractions collected. After gel analysis, the fractions were pooled. The gel filtration runs were then combined, resulting in approximately 20 ml. The sample was then dialyzed versus 25 mM Tris acid/25 mM Tris base, 10% glycerol, 1 mM EDTA, 10 mM imidazole and 1 mM DTT. Sample was removed from dialysis, centrifuged at 12,000×g for 30 min and loaded on to a 5 ml Q column equilibrated with the dialysis buffer. The column was run with a flow rate of 1 ml/min and 4 ml fractions of the flow through was collected and analyzed by SDS-PAGE. Samples were pooled, one-tenth volume of NaCl was added to the pool, and the samples were concentrated by centrifical ultrafiltration using a 10 kD cutoff membrane (Filtron). Sample analysis by SDS-PAGE, Coomassie Stain, showed purity greater than 97%. Gel filtration indicated the presence of a small amount of dimmers, which increased upon storage in the cold. Yields were generally between about 12 mg and 20 mg. All steps were done at 4° C.

In vitro Polymerase Assays. The substrate for in vitro polymerase assays was the M13 −47 sequencing primer annealed to single-stranded M13mp18 DNA (New England Biolabs). The −47 primer as end-labeled using T4 polynucleotide kinase and [$\gamma^{32}$P]ATP then annealed to the single-stranded M13mp18 DNA. The substrate was resuspended in 90 μl of buffer lacking dNTPs to a final concentration of 2 nM (see below) and 1.0 μg of enzyme. The mixture was incubated at room temperature for 5 min to allow the enzyme to bind the template-primer. The reaction was initiated by the addition of 10 μl of 0.2 mM dATP, 0.2 mM dCTP, 0.2 mM dGTP, and 0.2 mM dTTP. In a processivity assay, 0.5 units poly(rC):oligo (dG) was also included as a cold trap. The final concentrations of buffer in the reactions were: 25 mM Tris (pH 8.0), 75 mM KCl, 8.0 mM $MgCl_2$, 2.0 mM DTT, 10.0 mM CHAPS, 100 μg/ml acetylated bovine serum albumin (BSA), 10.0 μM of each DNTP in a final volume of 100 μl. After 10 min at 37° C., the reaction was terminated by extraction with an equal volume phenol/chloroform and the mixture was precipitated with isopropyl alcohol. The sample was resuspended in 10 μl loading dye and 4 μl loaded on a 6% sequencing gel. The products of the reaction were visualized by exposure to X-ray film. The DNTP curves were performed using the buffer described above and the indicated concentration of dNTPs, in the absence of poly(rC):oligo(dG). Reactions were incubated at 37° C. for 15 minutes.

The 3TCTP inhibition assays were performed using the M13 template and the −47 primer. The −47 sequencing primer was annealed to the single stranded M13mp18 DNA by heating to 95° C. and slowly cooling to room temperature. The template-primer was extended by adding 1.0 μg of RT in 25 mM Tris(pH 8.0), 75 mM KCl, 8.0 mM $MgCl_2$, 100 μg/ml BSA, 10 mM CHAPS, 10 μM each of dATP, dGTP, and dTTP, 2.0 μM [$\alpha$-$^{32}$P]dCTP, and the indicated concentrations of 3TCTP (Moravek Biochemicals, Brea, Calif.) in a 100 μl reaction volume. The mixture was incubated at 37° C. for 30 min, then halted by the addition of 3 ml of ice-cold trichloroacetic acid (TCA) and the precipitated DNA was collected by suction filtration through Whatman GF/C glass filters. The amount of incorporated radioactivity was determined by liquid scintillation counting.

Fidelity Assay. The fidelity assay used was that disclosed by Boyer and Hughes (J. Virol. 74:6494-6500 (2000), incorporated herein by reference). Briefly, plasmid Litmus 29 was obtained from New England BioLabs. The plasmid contains an M13 origin of replication and a restriction enzyme recognition site polylinker, including a recognition site for BamHI, 5' of the coding region for the LacZα-complementing fragment. Litmus 29 was linearized with HpaI, ligated to NotI linkers, and recircularized to make Litmus 29 (Not). The new NotI recognition sequence was located 3' of the lacZα-coding region.

Single-stranded uracil-containing DNA was formed by introducing the construct Litmus 29 (Not) into the Dut⁻ Ung⁻ male E. coli strain CJ236 (New England BioLabs). This bacterial strain introduced deoxyuracil residues into the plasmid DNA during replication. To generate single-stranded U-DNA Litmus 29 (Not), the helper phage M13K07 (New England BioLabs) was used according to the manufacturer's instructions. Briefly, 50 ml of Luria-Bertani medium supplemented with uridine (0.25 μg/ml) was inoculated with a colony of Litmus 29 (Not) in CJ236. The culture was incubated at 37° C. with agitation until the solution was slightly turbid. The helper phage M13K07 was added to a final concentration of $10^8$ PFU/ml. The culture was incubated at 37° C. with agitation for an additional 60 min. Kanamycin was added to a final concentration of 70 µg/ml, and the culture was incubated overnight at 37° C.

Bacteria were removed by sedimentation twice at 8,000 rpm for 10 min. One-fifth volume of 2.5 M NaCl-20% PEG (polyethylene glycol) 6000-8000 (NaCl-PEG) was added to the supernatant, and the solution was incubated on ice for 2 h. The phage particles were isolated by centrifugation at 8,000 rpm for 10 min. The pellet was resuspended in 1.6 ml of 10 mM Tris-Cl (pH8.0)-1.0 mM EDTA (TE) and divided into two tubes. The solution was cleared by centrifugation in a microcentrifuge at full speed to remove any trance of bacteria. $MgCl_2$ was added to a final concentration of 10 mM, and DNase was added to the solution to remove both contaminating bacterial and double-stranded phage DNA released by bacterial lysis. Intact phage particles were isolated by the addition of 200 µl of NaCl-PEG solution to each tube and centrifugation in a microcentrifuge for 5 min at full speed. The phage pellet was resuspended in 100 µl of TE and extracted three times with phenol-chloroform. After the addition of NaCl to a final concentration of 50 mM, the phage DNA was precipitated with 1 volume of isopropanol, then resuspended in 400 µl of $H_2O$ and stored at −20° C. The phage DNA can be further purified by use of a Qiagen M13 purification Kit or other standard protocol for the isolation of U-DNA.

The fidelity assay used a fidelity primer (5'-CCCATGGT-GAAGCTTGGAT CCACGATATCCTGCAGG-3'; SEQ ID NO: 16) which matches the sequence surrounding the BamHI recognition site in the Litmus 29 (Not) polylinker. For each fidelity assay, 2.5 µl from a 10.0-$A_{260}$/ml stock of fidelity primer was annealed to 1.0 µg of single-stranded U-DNA by heating and slow cooling. Each sample was adjusted to consist of 25 mM Tris-Cl (pH 8.0), 75 mM KCl, 8.0 mM $MgCl_2$, 2 mM dithiotreitol, 100 µg of bovine serum albumin per ml, 10 mM CHAPS (3-[(3-cholamidopropyl)-dimethylammonio]-1-propanesulfonate), and 20 µM each DATP, dCTP, dGTP, and dTTP. One microgram of reverse transcriptase to be tested (HIV-1 RT, PFV-RT, PFV D/A-RT and PFV D/A-RTV313M) was added, and the samples were incubated for 15, 20, 30 min, or longer at 37° C. The reactions were stopped by the addition of 1 volume of phenol-chloroform, followed by isopropanol precipitation with a 70% ethanol wash. The extended template primers were digested with BamHI and NotI, and the resulting fragments were fractionated on a 2% agarose gel. If an RT copied the lacZα portion of the template past the NotI recognition sequence, a band approximately 300 bp in size was visible in the gel. Primers that were not extended past the NotI site were annealed to phage DNA that was linearized with BamHI which migrated near the top of the gel. The BamHI/NotI fragment encoding LacZα was isolated from the gel and purified. These fragments were ligated into the B/N RT(His) construct (Boyer and Huges, supra), transformed into *E. coli* DH5α and plated onto NZY (10.0 g NZ amine, 5.0 g NaCl, 5.0 g yeast extract, and 2.0 g $MgSO_4$ per liter)-ampicillin plates supplemented with 5-bromo-4-chloro-3-indoyl-β-D-galactopyranoside (X-gal). The dark blue, light blue, and white colonies were counted. DNA was isolated from the light blue and white colonies and tested by digestion with BamHI and NotI. The 300 bp lacZα inserts were than sequenced.

Results

Efficacy of Reverse Transcriptase Inhibitors. The unique timing of Prototype Foamy Virus (PFV; previously designated SFVcpz(hu)) reverse transcription allows the virus to infect cells that were pre-treated with reverse transcriptase inhibitors, since infectious PFV particles already contain the viral DNA. However, PFV is unable to produce infectious particles from cells that are treated with inhibitor. This specific inhibition was demonstrated in previous studies with the inhibitor AZT, however not with the inhibitors 3TC and ddI (Yu et al. *J Virol.* 73:1565-1572 (1999)). To better understand the susceptibility of PFV, a more complete panel of HIV-1 RT inhibitors was tested.

In studies designed to measure the effect of adding RT inhibitors to target cells, FAB cells, which are BHK-derived cells that contain β-galactosidase driven by the FV LTR (Yu and Linial, *J. Virol.* 67:6618-6624 (1993)), were treated with inhibitor 4 hrs prior to the addition of PFV viral stock. Forty-eight (48) hours after infection, cells were stained with X-Gal staining solution and infectivity of the virus, as measured by viral titer was determined. The reverse transcriptase inhibitors 3TC, 3'-Azido-2',3'-dideoxy-5-methylcytidine (AzddMeC), 3'-azido-2',3'-dideoxyuridine (AzddU), AZT, 2',3'-didehydro-2',3'-dideoxythymidine (D4T), 2',3'-dideoxycytidine (ddC), beta-2',3'-dideoxy-5-fluoro-3'-thiacytidine (FTC), and phosphonoformate (PFA) were used in these experiments at the highest concentrations that demonstrated no cellular toxicity. All concentrations used were known to inhibit HIV-1 replication. None of the inhibitors had a dramatic effect on PFV infectivity, as predicted by the FV life cycle (Table 1).

To test the effects of the inhibitors on virus producing cells, FAB cells were infected with PFV at a multiplicity of infection (MOI) of 1, and 24 hrs after infection inhibitor was added. Forty-eight (48) hrs after infection, virus was harvested from these cells, and titered on fresh FAB cells. The titers revealed a range of inhibition, but only AZT demonstrated a specific decrease in infectivity of greater than 10 fold (Table 1).

It was not surprising that 3TC was unable to inhibit PFV replication given that the highly conserved YXDD (SEQ ID NO: 17) sequence in PFV RT is YVDD which is the same as the sequence of the resistant HIV-1 RT catalytic site. To determine whether mutating the RT sequence to YMDD might render PFV sensitive to 3TC, valine (V) was changed to a methionine (M) in the PFV RT YXDD motif to create the mutant PFV RT-V313M.

TABLE 1

Efficacy of Reverse Transcriptase Inhibitors

| Inhibitor | | Titer Relative to No-Drug Control | |
|---|---|---|---|
| | | Pretreated | Post-treated |
| No drug | | 100 | 100 |
| 3TC | 60 µM | 120 | 91 |
| AzddMeC | 25 µM | 70 | 13 |
| AzddU | 25 µM | 51 | 11 |
| AZT | 100 µM | 22 | <0.14 |
| D4T | 25 µM | 54 | 32 |
| ddC | 25 µM | 42 | 32 |
| FTC | 60 µM | 122 | 138 |
| PFA | 25 µM | 100 | 23 |

TABLE 2

Replication of HFV RT-V319M mutant in FAB cells

| Days post-transfection | Virus Titer (flu/ml) | | | |
|---|---|---|---|---|
| | WT HFV | V319M-CloneA | V319M-Clone B | Mock |
| 2 | $1.4 \times 10^3$ | $1 \times 10^1$ | $1 \times 10^1$ | $<10^1$ |
| 4 | $1.7 \times 10^4$ | $1 \times 10^1$ | $5 \times 10^1$ | $<10^1$ |
| 6 | $1.4 \times 10^4$ | $4 \times 10^1$ | $8 \times 10^1$ | $<10^1$ |
| 8 | $8.7 \times 10^3$ | $1 \times 10^1$ | $3 \times 10^1$ | $<10^1$ |
| 10 | | $3.6 \times 10^2$ | $4.9 \times 10^2$ | $<10^1$ |
| 12 | | $5.6 \times 10^3$ | $8.8 \times 10^3$ | $<10^1$ |
| 14 | | $1.5 \times 10^5$ | $1.7 \times 10^5$ | $<10^1$ |
| 16 | | $1.5 \times 10^5$ | $1.2 \times 10^5$ | $<10^1$ |
| 18 | | $2.9 \times 10^4$ | $2.0 \times 10^4$ | $<10^1$ |

Replication of RT-V313M. The effect on virus replication of the V to M mutation in PFV RT was determined by transfecting FAB cells with DNA of PFV RT-V313M(A) and (B), two independently derived clones. Two days after transfection, supernatants were collected and titered on fresh FAB cells. Surprisingly, the mutant virus showed an extremely low titer, indicating that very little infectious virus was being made with the mutant RT (Table 2). In an attempt to select for second-site mutations or reversions, the cells transfected with the mutant RTs were passaged until supernatants showed titers similar to wild-type levels. At two-day intervals, the supernatants were collected and titered on fresh FAB cells while the cells were split 1:3 and maintained. By day 12 the cells produced virus with titers similar to wild type PFV (Table 2).

Virus was isolated from the cell-free supernatants of day 14, when titers of the PFV RT-V313M viruses were at the highest level. RNA was extracted from virus and used in RT-PCR reactions designed to amplify the region of PFV pol encoding the V313M mutation. The RT-PCR products were used to isolate individual clones, which were then sequenced and analyzed for any changes from the original sequence. The sequence alignment of the individual clones and the original sequence revealed a two-nucleotide change at the ATG methionine codon to regenerate the valine codon present in wild type. The clones also had nonspecific single nucleotide changes, however none of these individual mutations were found in any other clones, suggesting that they were not second site mutations involved in reversion. Thus, it appears that PFV does not replicate if the RT has a methionine in the second residue of the YXDD motif (SEQ ID NO: 17).

Figure 2:
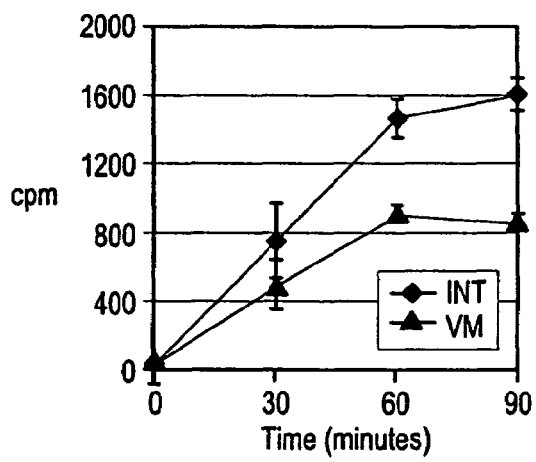
FIG. 2 depicts the virion-associated RT activity of PFV RT-V313M on a homopolymeric template. FAB cells were transfected with viral or irrelevant (mock) plasmid DNA, extracellular virions were harvested 4 days post-transfection and concentrated. RT activity was determined for each of the concentrated samples by measuring incorporation of a radiolabeled nucleotide on a poly (A);d(T) template primer over time. Each time point was normalized to the mode sample.

Virion-Associated Activity of PFV RT-V313M. The fact that the V313M mutation is located near the polymerase catalytic site suggested that this mutation might affect the catalytic activity of the enzyme. To test whether PFV RT-V313M had any exogenous polymerase activity, supernatants were collected from transfected FAB cells. Concentrated virions were used in an RT assay which measured the incorporation of radiolabeled nucleotide onto a polyA:oligo dT primer-template over the course of 90 minutes. As a positive control for this assay, another mutant virus, PFV-IN(−), which contains a wild type RT enzyme but has a mutation in the active site of Integrase (IN) making it replicative defective, was used. PFV-IN(−) is unable to produce infectious virus, similar to PFV RT-V313M, and therefore produced similar amounts of virus for comparison. A Western blot was performed on the IN(−) and the V313M concentrated virus particles to demonstrate that enzyme from similar numbers of viral particles were used in the assays. The plasmid pNEB193, which contains no viral sequences, was used as a negative control for normalization of the assays. The results from the RT assays demonstrate that the V313M mutant RT retains approximately 50% of wild type polymerase activity (FIG. 2). Given the dramatic effect this mutation had on replication, it was surprising to find a relatively modest decrease in RT-V313M activity.

RT-V313M Reverse Transcription Products in Cells. Since the mutant RT retained substantial polymerase activity, it was determined whether or not reverse transcription was completed in cells transfected with PFV RT-V313M. Because the PFV RT-V313M mutant did not replicate well, it was difficult to obtain significant quantities of virus or viral products in cells that were transfected using LIPOFECTAMINE. To increase the production of mutant viruses in transient transfections, the viral genome was placed under the control of the CMV promoter. Calcium phosphate transfection was used to introduce the CMV-driven viral clones into 293T cells. This technique greatly increased viral expression and simplified the analysis or replication-defective viruses.

Two different approaches were used, first was the detection of 2LTR circles using PCR combined with Southern blot analysis. 2LTR circles are a by-product of the completion of reverse transcription of the full-length linear viral DNA. A fraction of the full-length DNAs are joined by blunt-end ligation to form 2LTR circles. Primers were designed to hybridize to the 5' and 3' LTR regions such that polymerization would extend the primers to the ends of unintegrated linear viral DNA. If the cDNA is in a linear form or incomplete, no productive PCR product would be generated. However, when 2LTR circles are present, a specific PCR product is formed. Two positive controls containing wild type RTs were used including the IN(−) mutant described above and the FST4 mutant, which lacks the Env cleavage site. Neither mutant produces infectious virus, but both release particles that contain wild-type RT. The PolΔ5 mutant, which contains a large 500 bp deletion in the RT coding region, does not have a functional RT enzyme and consequently does not replicate in the RT coding region, was used as a negative control.

293T cells were transfected with the above described mutants and four days post-transfection genomic DNA was isolated. PCR products from 500 ng of cellular DNA were separated on agarose gels and transferred to a nylon membrane for Southern hybridization. A radiolabeled fragment of the PFV LTR region was used as the probe. The Southern blot showed that the PCR product specific for the 2LTR circle was present in all of the samples derived from transfections of viruses with a wild-type RT enzyme (WT, IN(−), and FST4), but was absent in samples derived from virus with the RT deletion (PolΔ5) and the RT-V313M virus. Since the positive control virus FST4 had a weaker signal than the wild type and IN(−) controls, the FST4 virus was used to determine the range of sensitivity for this assay. The genomic DNA from cells transfected with the FST4 virus was serially diluted 1000-fold (500 ng to 0.5 ng) and those samples were subjected to the PCR and Southern blot described above. 2LTR circles could be detected in a 100-fold dilution of the original sample, indicating that the production of 2LTR circles is at least 100-fold lower with the V313M mutant RT than with the wild type RT.

Figure 3:
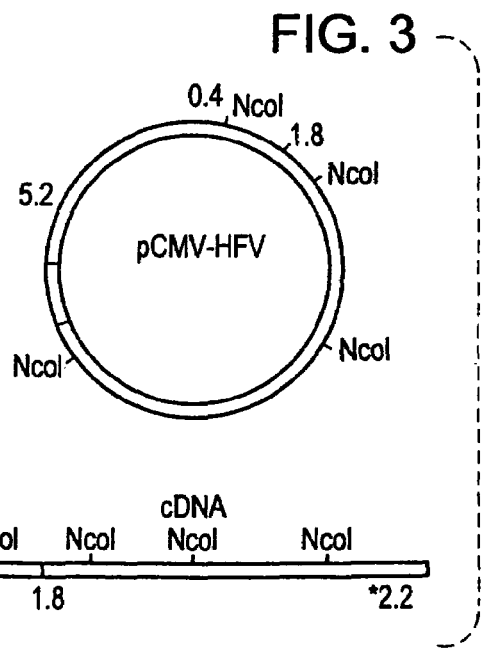
FIG. 3 depicts a diagram of NcoI sites in the viral plasmid used for transfection and predicted sizes of resulting products that hybridize to the probe. The shaded gray regions of the DNA indicate the location of the LTRs. The asterisk indicates the size of the fragment corresponding to the unique cDNA fragment.

The second approach employed to address whether or not the RT-V313M mutant was able to complete reverse transcription involved direct Southern blotting of the genomic DNA isolated from transfected 293T cells. The genomic DNA samples used in the 2LTR PCR experiments were digested with the restriction enzyme NcoI. This enzyme produces DNA fragments that allowed the distinction between the input plasmid DNA and the desired linear viral cDNA. A diagram of NcoI sites in the viral plasmid used for transfection and predicted sizes of resulting products that hybridize to the probe is provided as FIG. 3. After digestion, the DNA samples were fractionated on an agarose gel, transferred to a nylon membrane, and probed with the same radiolabeled PFV-LTR fragment used above. Detection of a 2.2 kb band corresponding to the 3' LTR of the cDNA product indicated the presence of viral cDNA in the transfected cells (FIG. 3). The blot demonstrated that cells transfected with either of the viruses that contain wild-type RT enzyme (WT and IN(−)) were undergoing reverse transcription and generated detectable amounts of cDNA. However, cDNA could not be detected in cells transfected with the PolΔ5 or V313M viruses. These results agree with the 2LTR results and demonstrate that although the RT-V313M has about 50% activity in an exogenous RT assay, it was unable to complete reverse transcription in an infected cell.

RT-V313M Activity in Vitro. In order to perform more detailed characterization of RT-V313M RT activity, a His-tagged version of the protein was produced in *E. coli* and purified over a nickel column as described above. In the context of the virus, reverse transcriptase is expressed as part of a larger Pol polyprotein, which also contains IN (integrase) and PR (protease). Unlike most other retroviruses, the foamy virus Pol undergoes a single cleavage event, which releases IN, leaving a PR-RT fusion protein. However, in some bacterial over-expression systems a second cleavage event between PR and RT has been reported (Pfrepper et al., *J. Virol.* 72-7648-7656 (1998)). To avoid this cleavage and the toxicity of PR in bacteria, the PR-RT fusion protein expressed in bacteria had a point mutation in the PR active site that inactivated the protease (Konvalinka et al., *J. Virol.* 69:7264-7268 (1995)). Expression plasmids with the mutation in the protease active site are designated D/A.

Figure 4:
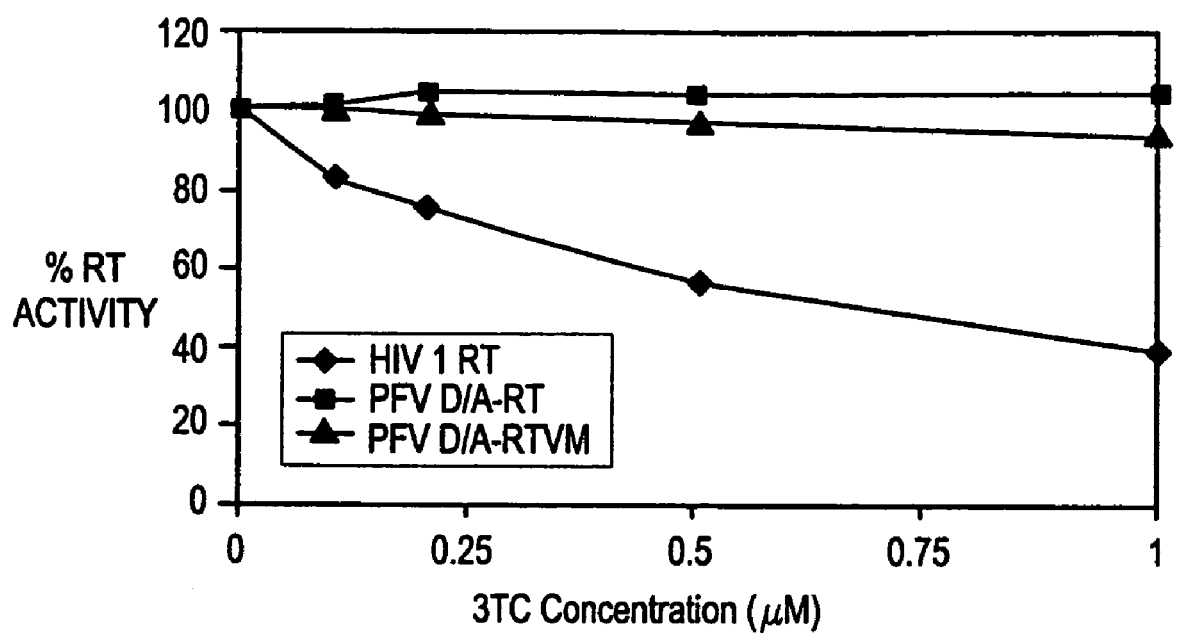
FIG. 4 depicts the 3TCTP inhibition curves for HIV-1, FV D/A, and FV D/A-RTVM recombinant RTs. Polymerization using a heteropolymeric template by purified recombinant RTs was measured by incorporation of radiolabeled dCTP in the absence or presence of 3TCTP at concentrations of 0.1 µM, 0.2 µM, 0.5 µM, 1.0 µM. HIV-1 RT (♦), FV D/A-RT (■), and FV D/A-RTVM (▲) were tested.

Using the purified recombinant PFV enzymes along with purified recombinant HIV-1 RT, it was first determined whether the FV RT-V313M was sensitive to 3TC. The M13 template and primer were annealed and then incubated with either FV D/A-RT, FV D/A-RT V313M, or HIV-1 RT and increasing concentrations of 3TCTP. Samples were TCA precipitated, bound to glass filters, and incorporation of radiolabeled dCTP was measured. In the absence of 3TCTP, it was found that both the V313M RT and the HIV-1 RT displayed about 35% polymerase activity of FV D/A RT. This was similar to the decrease in virion-associated RT activity observed for the V313M mutant virus described above. These levels of RT activity in the absence of drug were set at 100% activity for each recombinant RT. HIV-1 RT demonstrated sensitivity to 3TC, retaining only 37% of its activity at 1.0 μM 3TCTP (FIG. 4).

To compare the RT activities of the mutant and wild-type FV enzymes, standard kinetic analyses were performed using homopolymeric templates. However, the results obtained from these experiments suggested that a homopolymeric template may not be the appropriate substrate to study these enzymes. As an alternative method to compare the mutant and wild-type FV RTs, the effects of dNTP concentration on polymerization using a heteropolymeric template were examined. The M13 single stranded DNA template and radiolabeled primer were annealed, incubated with either HIV-1 RT, FV D/A-RT, or FV D/A-RTVM, and a reaction mixture containing increasing concentrations of each dNTP. The reaction was carried out for 15 min and then fractionated on a 6% sequencing gel. At concentrations above 1.0 μM most of the DNA synthesized by FV D/A-RT was too large to be measured accurately on a sequencing gel. The mutant FV D/A-RTVM was severely impaired in its polymerization at the lowest dNTP concentrations. However, the mutant did synthesize DNAs of 100 nt or longer at dNTP concentrations of 0.2 μM or greater and does not approach saturation until the highest dNTP concentrations. These results suggested that the $k_m$ of the V313M mutant might be in the about 5 to about 10 μM range. HIV-1 RT also approached saturation at the highest dNTP concentrations, which suggested a $k_m$ also in the about 5 to about 10 μM range, similar to the V313M RT mutant. To measure the size of the DNA products synthesized by FV D/A-RT more accurately, another polymerization assay was performed using an M13 template and the products were fractionated on a 1% alkaline agarose gel. DNAs up to 7 kb were synthesized in 20 min, but the rate of DNA synthesis was still increasing at dNTP concentrations greater than 20 μM. These data suggested that the $k_m$ of FV D/A-RT for dNTPs was higher than that of the mutant.

Because FV RT-V313M did not support the synthesis of full-length cDNA and the recombinant FV D/A-RTV313M protein demonstrated a significant decrease in primer extension, particularly at low dNTP concentrations, the processivity of the mutant FV enzyme was measured and compared to both wild type FV D/A-RT and HIV-1 RT. The −47 primer was end-labeled and then annealed to the single-stranded M13mp18 DNA. This radiolabeled primer-template was incubated with the purified HIV-1 RT, FV D/A-RT and FV D/A-RTV313M proteins to allow the enzyme to bind the primer-template. The reaction was initiated by the addition of all of the four dNTPs. In some reactions an unlabeled poly (rC):oligo(dG) cold trap was added. The cold trap was added in excess, and bound any RT proteins that dissociated from their original primer-template. Thus, the RT extension products produced in the presence of a trap indicated how far the enzyme was able to extend before it dissociated from the template.

The reactions were carried out for 10 minutes, followed by immediate phenol:chloroform extraction and isopropanol precipitation of the nucleic acid. The samples were then fractionated on a 6% sequencing gel. In the absence of the cold trap, the HIV-1 RT generated products of about 350 to about 600 nucleotides in length while the FV D/A RT generated products well above 600 nucleotides in length. The mutant FV D/A-RTV313M generated products of an intermediate length. In the presence of the cold trap, the HIV-1 RT demonstrated predominantly shorter products, however, the FV D/A-RT still generated mostly products longer than 600 bp. In contrast to the wild type FV RT the FV D/A-RTV313M enzyme did not generate products longer than 600 nt, but instead showed a range of shorter products, none of which were longer than 400 bp. These results demonstrated that wild type FV RT was a highly processive enzyme, producing large quantities of long products after only 10 minutes in the assay used. The inability of the FV D/A-V313M RT to generate longer products indicated that this enzyme was dramatically less processive than the wild type FV enzyme, although it was similar to HIV-1 RT. The substitution of methionine for valine in the YXDD motif affected processivity which might explain the inability of the mutant RT to complete reverse transcription. Foamy virus Reverse transcriptase appears to require valine in its catalytic site in order to maintain processivity, and consequently its ability to successfully complete reverse transcription. In addition, it appears that the FV RT has about a five-fold lower error rate than the rate that has been measured for HIV-1 RT.

DISCUSSION

The highly conserved YXDD (SEQ ID NO.: 17) motif contains two of the three aspartic acid residues that make up the RT active site (Julias, et al., *J. Virol* 75:6537-6546 (2001); Kohlstaedt et al., *Science* 256:1783-1790 (1995); Nanni et al., *Perspect Drug Discov. Des.* 1:129-150 (1993); Tantillo et al., *J. Mol. Biol.* 243:369-387 (1994)). The three-dimensional crystal structure of HIV-1 RT shows that the YXDD motif is located on the β9-β10 hairpin and is part of the dNTP biding site (Huang et al., *Science* 282:1669-1675 (1998); Jacobo-Molina et al., *Proc. Natl. Acad. Sci. USA* 90:6320-6324 (1993)). More specifically, the second variable residue (X) appears to interact with the ribose of the terminal primer nucleotide (Gao et al., *J. Mol. Biol.* 300:403-418 (2000); Sarafianos et a., *Proc. Natl. Acad. Sci. USA* 96:10027-10032 (1999); Tantillo et al., *J. Mol. Biol.* 243:369-387 (1994)). It has been postulated that this interaction between the second (X) residue and the primer may be important for affinity to the template-primer, and different residues in the second position may alter flexibility of the dNTP binding pocket, leading to changes in the behavior of the enzyme (Boyer and Hughes, *Antimicrobial Agents and Chemotherapy* 39:1624-1628 (1995); Ding et al., *Biopolymers* 44:125-138 (2000); Gao et al., *J. Mol. Biol.* 300:403-418 (2000); Harris et al., *J. Biol. Chem.* 273:3324-3334 (1998); Sarafianos et al., *Proc. Natl. Acad. Sci. USA* 96:10027-10032 (1999); Tantillo et al., *J. Mol. Biol.* 243:369-387 (1994)). Therefore, it is likely that the size and/or the hydrophobicity of the amino acid side chain of the second residue in the YXDD motif can influence the catalytic activity of the polymerase RT. Changes in the YXDD motif can also alter the active site structure and/or lead to the repositioning of the template-primer in such a way that the RT/DNA complex incorporates normal dNTPs less efficiently. Such an altered structure could be less stable, and thus PFV RT-V313M could dissociate more easily from its nucleic acid substrate than the wild-type enzyme, reducing processivity.

In contrast to PFV, HIV-1 with the 3TC resistance mutation YVDD (M184V) replicates almost as well as wild-type (YMDD) (Schinazi et al., *Antimicrobial. Agents and Chemotherapy* 37:875-881 (1993)). In vitro, HIV-1 M184V RT displays 75% of the activity of wild type RT and has reduced procesivity (Boyer and Hughes, *Antimicrobial. Agents and Chemotherapy* 39:1624-1628 (1995)). Further, MLV with the mutant YMDD motif (V223M) retains 20% of wild type activity yet it is still able to replicate with only a 10-fold decrease in titer compared to wild type (Halvas et al., *J. Virol.* 74:312-319 (2000)). In vitro, recombinant wild type and YMDD MLV RTs show similar polymerase activities and have similar extension abilities (Boyer et al., *J. Virol.* 75:6321-6328 (2001)). Thus, although mutations in the YXDD motif affect the polymerase activities of the HIV-1 and MLV, these viruses are still able to replicate with either M or V present in the variable position of the YXDD motif; the architecture of the active site for both HIV-1 and MLV must be able to tolerate either amino acid residue. The data provided above demonstrates that the same is not true for PFV RT. A PFV RT with YMDD (V313M) could not support productive replication of the virus. The mutant virus rapidly reverted to YVDD despite the fact that the mutant RT retained approximately 50% of wild type activity.

Conventional retroviruses generate both Gag and Gag-Pol fusion proteins, at a ratio of about 20:1. The result is a virus particle that contains approximately 50-75 Pol proteins per particle (Vogt and Simon, *J. Virol.* 73:7050-7055 (1999)). PFV Pol is expressed from its own spliced message, and the mechanism for packaging the Pol protein is unclear. In FV infected cells, the Pol protein is sufficiently abundant that it can be easily detected by Western blot. However, we have been unable to detect Pol in virus particles by Western blot or by radioimmunoprecipitation, although in more recent work using a monoclonal antibody to Pol, it has been detected. There is some evidence for a cis-acting RNA sequence at the 5' end of the FV genome (CASI) that is not involved in RNA packaging but is required for PR activity (Heinkelein et al., *J. Virol.* 74:3141-3148 (2000)) and for Pol packaging. If Pol must bind to a specific region of the RNA for encapsidation, this would limit the number of molecules that can be incorporated.

A low number of Pol molecules in a viral particle places a special burden on PFV RT, relative to other retroviral RTs. One or two FV RT would have to accomplish the same task carried out by the 50 to 75 RTs present in other retroviral particles (Vogt and Simon, *J. Virol.* 73:7050-7055 (1999)). In order to overcome this disadvantage, FV RT would necessarily be a particularly efficient polymerase, and our results suggest that this is the case. It is likely that a moderate decrease in RT activity in viruses such as HIV-1 and MLV does not have a dramatic effect on replication because there are a relatively large number of RTs in the particle that can collaborate to carry out reverse transcription (Julais et al., *J. Virol.* 75:6537-6546 (1999); Telesnitsky and Goff, *EMBO J.* 12:4433-4438 (1993)). In the case of PFV, a minor decrease in RT activity could be much more detrimental if only one or two RTs were responsible for reverse transcription.

As might be expected if PFV requires a highly active RT, the above results also show that FV RT is an extremely processive. In the processivity assay, wild type PFV RT was able to generate products that were significantly longer than 600 nt in 10 min. HIV-1 RT is much less processive, generating products ranging from 100 to about 400 nt in length. This high level of processivity for PFV should effectively compensate for the small number of Pol proteins in a virion. The above results support the idea, showing that the mutant V313M, which cannot replicate, has a decrease in processivity compared to wild type PFV RT. Yet, in vitro the mutant enzyme has a processivity that is comparable to, or slightly better than that of HIV-1 RT. Thus, FV is not able to replicate with a mutant RT that has a processivity similar to that of HIV-1.

The discovery of the high processivity of isolated PFV reverse transcriptase provides a particularly useful reagent for use in molecular biology. The enzyme is particularly useful for the in vitro production of RNA from a polynucleotide sequence. For example the enzyme can be used in place of typical reverse transcriptase in PCR kits and for other methods commonly used for the production of RNA. The use of the foamy virus reverse transcriptase-protease fusion protein with a functionally inactivated protease provides a means for making large quantities of the fusion protein, such as by a recombinant bacterial host cell, without the cleavage of the fusion protein typically seen in these systems.

Although the foregoing invention has been described in some detail by way of illustration and example for purposes of clarity of understanding, it will be obvious that certain changes and modifications may be practiced within the scope of the appended claims. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. An isolated nucleic acid encoding a polyprotein consisting of foamy virus protease-reverse transcriptase having substantially reduced protease activity as compared with wild-type protease-reverse transcriptase and a highly processive reverse transcriptase, wherein the foamy virus protease-reverse transcriptase polyprotein comprises a mutation in the aspartic acid residue in the protease catalytic site, and wherein the highly processive reverse transcriptase can produce a nucleotide product of more than 600 basepairs in 10 minutes.

2. The nucleic acid of claim 1, wherein the nucleic acid encodes a modified simian, cow, or human foamy virus protease-reverse transcriptase.

3. A vector comprising a nucleic acid encoding a polyprotein consisting of foamy virus protease-reverse transcriptase having substantially reduced protease activity as compared with wild-type protease-reverse transcriptase and a highly processive reverse transcriptase, wherein the foamy virus protease-reverse transcriptase polyprotein comprises a mutation in the aspartic acid residue in the protease catalytic site, and wherein the highly processive reverse transcriptase can produce a nucleotide products of more than 600 basepairs in 10 minutes.

4. A recombinant host cell comprising a vector of claim 3.

5. A kit for the preparation of cDNA comprising an isolated foamy virus protease-reverse transcriptase polyprotein having a highly processive reverse transcriptase activity, and substantially reduced protease activity as compared with wild-type protease-reverse transcriptase, wherein the foamy virus protease-reverse transcriptase polyprotein comprises a mutation in the aspartic acid residue in the protease active site, a primer, an oligonucleotide template, deoxyribonucleotide bases, buffers sufficient for reverse transcription and a container and wherein the highly processive reverse transcriptase can produce a nucleotide product of more than 600 basepairs in 10 minutes.

* * * * *

UNITED STATES PATENT AND TRADEMARK OFFICE
CERTIFICATE OF CORRECTION

| | | |
|---|---|---|
| PATENT NO. | : 7,560,117 B2 | |
| APPLICATION NO. | : 10/478442 | |
| DATED | : July 14, 2009 | |
| INVENTOR(S) | : Stephen Hughes et al. | |

It is certified that error appears in the above-identified patent and that said Letters Patent is hereby corrected as shown below:

Page 1 of patent, paragraph (73), please insert second Assignee:

-- The Government of the United States of America as Represented by the Secretary of the Department of Health and Human Services, Rockville, MD (US) --

Signed and Sealed this

Eighteenth Day of August, 2009

David J. Kappos
*Director of the United States Patent and Trademark Office*

UNITED STATES PATENT AND TRADEMARK OFFICE
CERTIFICATE OF CORRECTION

PATENT NO.       : 7,560,117 B2  Page 1 of 1
APPLICATION NO.  : 10/478442
DATED            : July 14, 2009
INVENTOR(S)      : Stephen Hughes et al.

It is certified that error appears in the above-identified patent and that said Letters Patent is hereby corrected as shown below:

Column 1, line 16, please delete

"This work was supported by a grant from the National Cancer Institute (No. CA18282 and CA09229)"

And insert

--This invention was made in part with Government support under grant numbers CA18282 and CA09229 awarded by the National Cancer Institute. The Government has certain rights in the invention.--

Signed and Sealed this

Seventeenth Day of November, 2009

David J. Kappos
*Director of the United States Patent and Trademark Office*

SEQUENCE LISTING

<160> NUMBER OF SEQ ID NOS: 19

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Forward
      primer pol V313A.

<400> SEQUENCE: 1
ctaatgtaca agtgtatatg gatgatatat acttaagcca tg                              42

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Reverse
      primer Int(-) pL2-Sub2.

<400> SEQUENCE: 2
ccccaggctt tacactttat g                                                     21

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: RT-PCR
      forward primer pol1441t.

<400> SEQUENCE: 3
ccaacactct gctggtattt tagctacta                                             29

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: RT-PCR
      reverse primer pol2351.

<400> SEQUENCE: 4
cagctgacaa atttggacgt ccg                                                   23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Forward
      primer pol1548.

<400> SEQUENCE: 5
ggttaacagc atttacctgg caag                                                  24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer
      350R.

<400> SEQUENCE: 6
agaaagggtc catctgagtc ac                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer
      546F.

<400> SEQUENCE: 7
gattaaggta tgaggtgtgt gg                                              22

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: 5' PCR
      primer protease.

<400> SEQUENCE: 8
gcggcgccat ggcgaatcct cttcagctgt tacagccgct tccggcgg                  48

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: 3' PCR
      primer protease.

<400> SEQUENCE: 9
gcggcgcctt gaggaagacg tgtccaacaa tactgtttac c                         41

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: 5' PCR
      primer RNaseH.

<400> SEQUENCE: 10
gcggcgggat ccgctttacc cattagtgga taacatggat gac                       43

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence: 3' PCR primer
   RNaseH.

<400> SEQUENCE: 11
gcggcggaat tcgcgctaat attgtttggg atatcctttt atataatgac cctg           54

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide 1.

<400> SEQUENCE: 12

-continued atcccaaaca atattcttcc catcatcacc accatcatta gtaggtaccc g            51

<210> SEQ ID NO 13
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide 2.

<400> SEQUENCE: 13
aattcgggta ccttactaat gatggtggtg atgatgggaa gaatattgtt tgggat       56

<210> SEQ ID NO 14
<211> LENGTH: 4
<212> TYPE: PRT
<213> ORGANISM: Foamy virus

<400> SEQUENCE: 14

Pro Lys Gln Tyr
  1

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: His tag
      added to foamy virus protease C-terminus.

<400> SEQUENCE: 15

Pro Lys Gln Tyr Pro Ser Ser Gly His His His His His His
  1               5                  10

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Fidelity
      primer

<400> SEQUENCE: 16
cccatggtga agcttggatc cacgatatcc tgcagg                             36

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Foamy virus
      x=Val or Met.

<400> SEQUENCE: 17

Tyr Xaa Asp Asp
  1

<210> SEQ ID NO 18
<211> LENGTH: 5
<212> TYPE: PRT
<213> ORGANISM: Foamy virus

<400> SEQUENCE: 18

Met Asn Pro Leu Gln
  1               5

```
<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Introduced
      NacI site at start of foamy virus protease.

<400> SEQUENCE: 19

Met Ala Asn Pro Leu Gln
 1               5
```